(12) United States Patent
Gwon et al.

(10) Patent No.: US 7,794,697 B2
(45) Date of Patent: Sep. 14, 2010

(54) ENHANCEMENT OF LENS REGENERATION USING MATERIALS COMPRISING POLYSILOXANE POLYMERS

(75) Inventors: Arlene Gwon, Irvine, CA (US); Sverker Norrby, Leek (NL); Thomas Terwee, Roden (NL); Steven Koopmans, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 171 days.

(21) Appl. No.: 11/740,677

(22) Filed: Apr. 26, 2007

(65) Prior Publication Data
US 2007/0219633 A1 Sep. 20, 2007

Related U.S. Application Data

(63) Continuation-in-part of application No. 10/881,426, filed on Jun. 30, 2004.

(60) Provisional application No. 60/745,825, filed on Apr. 27, 2006.

(51) Int. Cl.
*A61K 31/74* (2006.01)

(52) U.S. Cl. .................................. 424/78.08

(58) Field of Classification Search .................. None
See application file for complete search history.

(56) References Cited

U.S. PATENT DOCUMENTS

| | | | |
|---|---|---|---|
| 5,213,579 A | 5/1993 | Yamada et al. | |
| 5,627,162 A | 5/1997 | Gwon et al. | |
| 5,681,825 A | 10/1997 | Lindqvist et al. | |
| 5,792,103 A | 8/1998 | Schwartz et al. | |
| 6,066,172 A | 5/2000 | Huo et al. | |
| 6,440,911 B1 * | 8/2002 | Bettiol et al. | 510/137 |
| 6,558,688 B2 | 5/2003 | Saishin et al. | |
| 6,945,971 B1 | 9/2005 | Gwon | |
| 7,278,990 B2 | 10/2007 | Gwon | |
| 2002/0185139 A1 | 12/2002 | Soll | |
| 2003/0130324 A1 | 7/2003 | Mcavoy et al. | |
| 2004/0039399 A1 * | 2/2004 | Norrby et al. | 606/107 |
| 2004/0086479 A1 | 5/2004 | Grinstaff et al. | |
| 2004/0258729 A1 | 12/2004 | Czemuszka et al. | |
| 2005/0037491 A1 | 2/2005 | Mistry et al. | |
| 2005/0191322 A1 | 9/2005 | Norrby | |
| 2006/0002981 A1 | 1/2006 | Gwon | |
| 2006/0083732 A1 | 4/2006 | Gwon | |
| 2006/0094643 A1 | 5/2006 | Svirkin et al. | |
| 2006/0134173 A1 * | 6/2006 | Liu et al. | 424/427 |
| 2007/0239274 A1 | 10/2007 | Kellan | |

FOREIGN PATENT DOCUMENTS

| | | |
|---|---|---|
| WO | 9214420 | 9/1992 |
| WO | WO 9940933 A1 | 8/1999 |
| WO | WO 0108603 A1 * | 2/2001 |
| WO | WO 03096875 | 11/2003 |
| WO | 2005107649 A2 | 11/2005 |
| WO | WO 05107649 A2 | 11/2005 |
| WO | 2006010009 A2 | 1/2006 |
| WO | WO 06019524 A1 | 2/2006 |
| WO | WO 06069012 A2 | 6/2006 |

OTHER PUBLICATIONS

Gwon et al. Induction of de novo synthesis of crystalline lenses in aphakic rabbits. Exp. Eye Res. 1989, vol. 49, 913-926.
Gwon et al. A histologic study of lens regeneration in aphakic rabbits. Investigative Ophthalmology & Visual Science. Mar. 1990, vol. 31, No. 3.
Gwon et al. Lens regenertaton in juvenile and adult rabbits measured by image analysis. Investigative Ophthalmology & Visual Science. Jun. 1992, vol. 33, No. 7.
Gwon et al. Lens regeneration in New Zealand albino rabbits after endocapsular cataract extraction. Investigative Ophthalmology & Visual Science. May 1993, vol. 34, No. 6.
Gwon et al. Restoring lens capsule integrity enhances lens regeneration in New Zealand albino rabbits and cats. J. Cataract Refract. Surg. Nov. 1993, vol. 19.
Gwon et al. Focal laser photophacoablation of normal and cataractous lenses in rabbits: preliminary report. J. Cataract Refract. Surg. May 1995, vol. 21.
Gwon et al. Intralenticular implant study in pigmented rabbits: opacity lensmeter assessment. J. Cataract Refract. Surg. Feb. 1999, vol. 25.
Mayer. Ueber die Reproduction der Krystallinse. Journal der Chirurgie und Augen-Heilkunde. 1982, 17:524.
Gwon et al. Restoration of lens capsule integrity enhances lens regeneration in New Zealand albino rabbits. Association for Research in Vision and Ophthalmology. May 1992.
Randolph. The regeneration of the crystalline lens: an experimental study. John Hopkins Hospital Reports. 1900, 9:237.
Stewart. Further observations on regenerated crystalline lenses in rabbits, with special reference to their refractive qualities. Trans Ophthalmol Soc UK. 1960, 80:357.
Arlene Gwon et al., "Lens Regeneration in New Zealand Albino Rabbits After Endocapsular Cataract Extraction," Invest Ophth, pp. 2124-2129, 1993, vol. 34.
Dover J. S. et al., "Clinical Use of Restylane," pp. 5-7, 2005, vol. 10 (1).
Fechner, "Efficacy of hyaluronidase [3]", Archives of Ophthalmology 2000 United States, pp. 445-446, 2000, vol. 118 (3).
Fechner, "Intraocular use of hyaluronidase to dissolve sodium hyaluronic acid," Journal of Refractive Surgery 1997 United States, pp. 502-503, 1997, vol. 13 (6).

(Continued)

*Primary Examiner*—Michael G Hartley
*Assistant Examiner*—Paul Dickinson

(57) ABSTRACT

The present invention addresses the treatment of ocular conditions by the enhancement of lens regeneration. Enhancement of lens regeneration is accomplished by the administration of a composition comprising a polysiloxane polymer having functional acryl groups useful in the preparation of intraocular lenses (IOLs).

5 Claims, 3 Drawing Sheets

OTHER PUBLICATIONS

Friess, "European Journal of Pharmaceutics and Biopharmaceutics," pp. 113-136, 1998, vol. 45 (2).

Gwon A. et al., "Tissue engineering of the lens, Suppl S,XP008076915 & Annual Meeting of the Association-For-Research-In-Vision-And-Oph Thalm Ology; Ft Lauderdale, FL, USA; May 01-05, 2005 ISSN: 0146-0404 the whole document," pp. 2871, 2005, vol. 46.

Healon® electronic package insert of 2003, accessed via http://home.intekom.com/pharm/genop/healon.html on Jan. 13, 2010.

Henry J. J., "The cellular and molecular bases of vertebrate lens regeneration," internationl Review of Cytology, Academic Press, pp. 195-265, 2003, vol. 228.

Nagineni et al., "Human Fetal Lens Epithelial Cells in Culture an In-Vitro Model for the Study of Crystailin Expression and Lens Differentiation," Current Eye Research, IRL Press, Oxford, GB, pp. 285-291, 1989, vol. 8 (3).

Nissan Pilest, "Perlane for Deep Wrinkles, Mid-Dermal Filler for moderate to Severe Facial Folds and Wrinkles: Scar Correction, Internet website: http://www.totaidermatology.com/pages/perlane.html," pp. 1-5.

Puhl et al., "Intra-articular hyaluronan treatment for osteoarthritis,"Annals of the Rheumatic Diseases, pp. 438-441, 1997, vol. 56.

Thomas S. C. et al., "Hyaluronic acid and its effect on postoperative adhesions in the rabbit flexor tendon. A preliminary look,"Clin Orthop Relat Res, 1986, vol. 206, pp. 281-9.

Voelker et al, Comparison of the proliferative effect of hyaluronic acid and methylhydroxypropyl-cellulose on cultured bovine lens epithelial cells, XP008076900 & 1996 Annual Meeting of the Association for Research in Vision and Ophthalmology; Fort Laude.

* cited by examiner

ENHANCEMENT OF LENS REGENERATION USING MATERIALS COMPRISING POLYSILOXANE POLYMERS

CROSS REFERENCES TO RELATED APPLICATIONS

The present application claims priority to Provisional Application No. 60/745,825 filed Apr. 27, 2006, and is a Continuation-in-Part of U.S. application Ser. No. 10/881,426, filed Jun. 30, 2004.

FIELD OF THE INVENTION

The present invention addresses the treatment of ocular conditions by the enhancement of lens regeneration. Enhancement of lens regeneration is accomplished through the administration of a composition comprising a polysiloxane polymer having functional acryl groups that is useful in the preparation of intraocular lenses (IOLs).

BACKGROUND OF THE INVENTION

A cataract is the clouding of a natural eye lens, the part of the eye that focuses light onto the retina to produce clear, sharp images. The lens is contained in a sealed bag or capsule. As old lens cells die they become trapped within the capsule, and, over time, the accumulation of these cells causes the lens to cloud, so that light is no longer focused properly onto the retina and images appear blurred or fuzzy. For most people, cataracts are a natural result of aging.

A process called extracapsular cataract extraction with implantation of an intraocular lens (IOL) is currently the most common method for the treatment of cataracts. This process involves removing the natural dysfunctional lens and replacing it with an artificial lens. This procedure is less than ideal, however, because the current synthetic IOLs are unable to accommodate appreciably, and secondary opacification of the posterior capsule (i.e. secondary cataracts) is a common occurrence following the procedure.

Importantly, after removal, in some situations eye lenses can regenerate over time. Ideally then, if a regenerated natural lens could replace a suitable biodegradable material, the reformed regenerated lens could have the same or similar natural focusing power as the normal young lens and could be able to accommodate visually. Alternatively, if naturally regenerating lens epithelial cells could be directed to grow in a regularly organized pattern around a suitably flexible and biocompatible polymeric lens, the resultant bilenticular system might also be able to accommodate. Therefore, there is a need in the art for a regenerated lens (with or without a suitably flexible and biocompatible polymeric lens) which would have properties of the natural lens including clarity, protein content, histology, focusing power, spectral transmission, accommodative ability, configuration, shape and structure.

One approach to forming a lens following cataract extraction has been to use accommodative refill lenses. Accommodative refill lenses are created by injecting low viscosity liquids (such as silicone oils or low temperature vulcanizing (LTV) silicone elastomers) into the len's capsular bag through a small incision. After injection, these low viscosity liquids polymerize under forming pressure to create a lens of the required shape. This technique uses the form of the capsular bag as a mold. Various drawbacks associated with this technique remain to date, however, preventing its beneficial use in all patients. The present invention provides beneficial methods of using new materials to create accommodative refill lenses and to enhance natural lens regeneration.

SUMMARY OF THE INVENTION

The present invention provides methods of enhancing lens regeneration using materials comprising polysiloxane polymers. Surgeons or researchers can inject the material into a capsular bag to form a lens or scaffold onto and around which lens cells can regenerate and organize.

Specifically, in one embodiment according to the present invention the invention is a method comprising enhancing regeneration of lens cells in a mammal after endocapsular extraction by filling a lens capsule bag of the mammal with an injectable lens material comprising a polysiloxane polymer wherein the injectable lens material has a viscosity for being injected through standard cannula and the polysiloxane polymer has functional acryl groups at terminal ends of the polymer.

In another embodiment of the methods, the endocapsular extraction occurs through a capsulorrhexis that is 3 millimeters or less.

Embodiment of the presently described methods can also further comprise one or more of: (i) inserting a foldable intraocular lens into the capsule bag of the mammal; (ii) positioning a contact lens or similar polymeric material in the form of a permeable or semi-permeable disc shaped lens between the anterior capsule and the injectable lens material; (iii) administering hyaluronic acid to the capsule bag of the mammal; (iv) administering hyaluronidase to the capsule bag of the mammal; and (v) inserting at least one collagen patch in the capsule bag of the mammal.

In another embodiment of the methods, the injectable lens material further comprises a photoinitiator and is capable of being photopolymerized into a solid intraocular lens.

In yet another embodiment of the methods, the polysiloxane polymer has a backbone of the general formula:

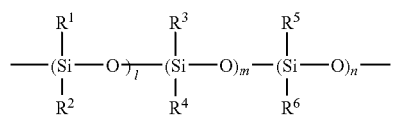

wherein $R^1$ and $R^2$ are independently $C_1$-$C_6$ alkyl; $R^3$ is phenyl; $R^4$ is phenyl or $C_1$-$C_6$ alkyl; $R^5$ is $CF_3$ $(CH_2)_x$ wherein x is 1-5; $R^6$ is $C_1$-$C_6$ alkyl or fluoroalkyl; l is in the molar fraction range of 0 to 0.95; m is in the molar fraction range of from greater than 0 to 0.7; and n is in the molar fraction range of from greater than 0 to 0.65.

The present invention also includes kits. Kits according to the present invention can comprises instructional materials and one or both of (i) a polysiloxane polymer; and (ii) a photocurable polysiloxane polymer and wherein the kit can also comprise one or more of (i) hyaluronic acid; (ii) hyaluronidase; (iii) a collagen patch; (iv) an intraocular lens; and (v) a contact lens or similar polymeric material in the form of a permeable or semi-permeable disc shaped lens. The instructional materials of these kits instruct the use of the included components in enhancing the regeneration of lens cells. In alternative embodiments, the instructional materials can also direct that the endocapsular extraction occurs through a capsulorrhexis that is 3 millimeters or less in length.

In another embodiment of the kits, the polysiloxane polymer has a backbone of the general formula:

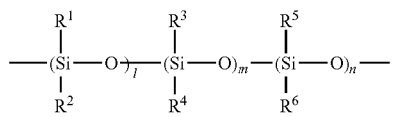

wherein $R^1$ and $R^2$ are independently $C_1$-$C_6$, alkyl; $R^3$ is phenyl; $R^4$ is phenyl or $C_1$-$C_6$ alkyl; $R^5$ is $CF_3$ $(CH_2)_x$ wherein x is 1-5; $R^6$ is $C_1$-$C_6$ alkyl or fluoroalkyl; I is in the molar fraction range of 0 to 0.95; m is in the molar fraction range of from greater than 0 to 0.7; and n is in the molar fraction range of from greater, than 0 to 0.65.

DEFINITION OF TERMS

Enhance lens regeneration: As used herein, "enhance lens regeneration" and variants of the same phrase include increasing the probability of a lens regenerating after extracapsular lens extraction wherein the lens will have less haze, less striae or fewer folds than it otherwise would have had without a described treatment or is a regenerative lens that is more clear than it otherwise would have been with a described treatment.

Functional acryl groups: As used herein, "functional acryl groups" include polysiloxane molecules having functional groups attached thereto including an acryl group moiety, so as to become acryl-bearing, by acryl attachment to the siloxane monomers of the polysiloxane backbone, its terminal ends, or both. The acryl groups in these functional groups can be linked to the silicone atoms by spacers. Examples of functional acryl groups include, without limitation, acrylamidopropyl, methacrylamidopropyl, acryloxyhexyl and methacryloxyhexyl. In one embodiment, the functional acryl groups are attached to the terminal ends of polysiloxane molecules, as exemplified by, without limitation, acrylamidopropyl-, methacrylamidopropyl-, acryloxyhexyl- and methacryloxyhexyl-terminated polysiloxanes. Those skilled in the art can consider numerous such alternatives which maintain the basic function of having an acryl group for subsequent crosslinking/polymerization of the polysiloxane molecules into larger network together with a photoinitiator. In the same manner it is also to be understood that the meaning of acryl group includes acryl or substituted acryl, such as, without limitation, methacryl, moieties attached through a variety of linkages including ester, amide and urethane linkages, or functional analogues of acryl capable of undergoing crosslinking reactions with a photoinitiator.

DETAILED DESCRIPTION

The present invention is based on the concept that the natural lens is capable of controlled or enhanced organic cellular or biological regeneration following endocapsular lens and/or cataract extraction. In various embodiments, the present invention provides methods to contribute to the production of a regenerated lens with properties similar to that of the natural lens, including, without limitation, clarity, protein content, histology, focusing power, spectral transmission and accommodative ability. In one embodiment, the natural regenerating lens tissue can be directed to grow in a more natural or regular pattern around a suitably flexible and biocompatible polymeric lens.

Figures 1, 2:
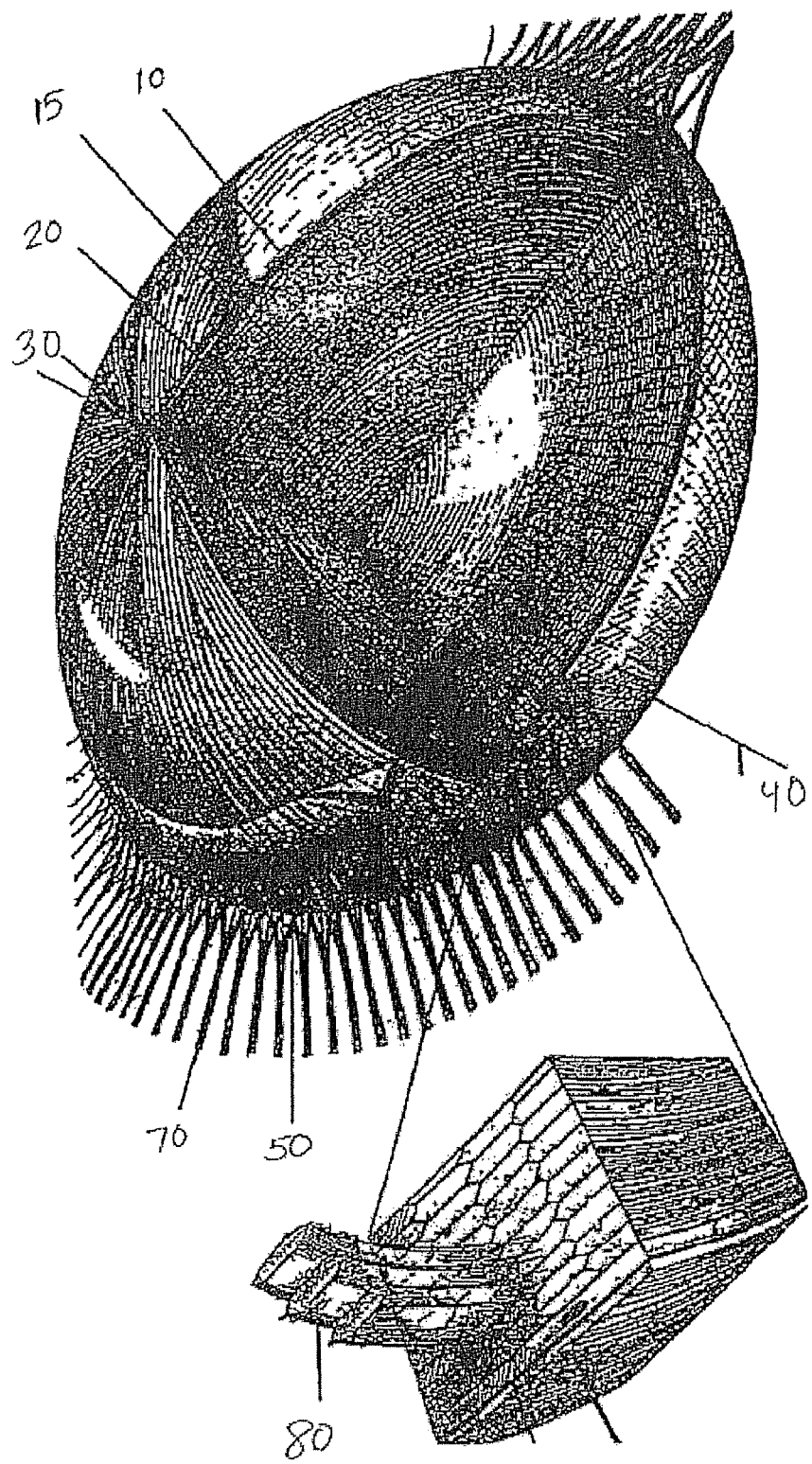
FIG. 1 illustrates the gross morphology of the lens fibers generated in the cortex in accordance with an embodiment of the present invention.
FIG. 2 illustrates a lens fiber depicted in FIG. 1 in accordance with an embodiment of the present invention.

FIG. 1 depicts the human lens and the gross morphology of the lens fibers generated in the cortex 15. FIG. 1 also depicts the capsule 10, nucleus 20, zonule 70, anterior pole 30, equator 50 and optical axis 40 of the lens. These regenerated lens fibers originate as epithelial cells and elongate into ribbon-like nucleus-free lens components. The cross sections of these lens components are hexagonal in shape. FIG. 2 depicts a closer view of a lens fiber 80, which has a hexagonal cross-section.

The concept of implanting a suitably flexible polymeric lens compatible with naturally regenerating lens tissue was previously suggested by studies in which Acuvue® contact lenses (etafilcon A, 58% H20; available from Johnson & Johnson Vision Care, Inc., Jacksonville, Fla.) were modified for intralenticular implantation in the rabbit eye. While normal regeneration was noted in one eye, the results were inconsistent and the nucleus of most regenerated lenses contained a star-shaped opacity related to the irregular growth pattern and misalignment of the earliest lens fibers.

In numerous studies, lenses that have been regenerated following endocapsular lens extraction in New Zealand Albino rabbits have been irregular in shape, appearing primarily doughnut-shaped. The newly formed lenses are irregular in shape as a result of the lack of lens growth at the site of the anterior capsulotomy and its adhesion to the posterior capsule. These regenerated lenses have had variable translucency because of irregular alignment of newly formed fibers, which may partly result from irregular proliferation of cells in zones of wrinkling or folding of the lens capsule in the early postoperative period. To improve the transparency of the regenerated lenses and their therapeutic utility, investigators have attempted to mimic the embryonic environment with limited success.

The various embodiments of the present invention reaffirm past findings in the art showing lens regeneration and demonstrate that regeneration of the lens can be enhanced through the use of polysiloxane polymer containing compositions. Certain embodiments according to the present invention also incorporate the use of hyaluronic acid to further enhance lens regeneration. Embodiments according to the present invention can also enhance lens regeneration by restoring lens capsule integrity following the administration of polysiloxane polymer containing compositions.

EXAMPLES

The following in vivo studies evaluated the use of polysiloxane polymers following endocapsular lens extraction in young and old New Zealand white rabbits.

General Materials

The polysiloxane polymer material used in the presently described studies was obtained from AMO (Groningen, Holland) and corresponded to composition AS4-11, CS0402014. Silicone plugs (4.5 mm) were also obtained from AMO (Groningen, Holland). "Shark Tooth" Phaco needles, (LAMINAR® Flow Phaco Tip15°/45°) and infusion sleeve (20 gauge, OPO154520L) were also obtained from AMO (Santa Ana, Calif.). Healon 5 was obtained from AMO (Uppsala, Sweden).

General Methods

The general health and acceptability of animals used in the following studies was established prior to surgery. A total of 7 New Zealand white rabbits were used in three studies. During surgery, rabbits were anesthetized with about 5 mg/kg xylazine and about 50 mg/kg ketamine HCl, intramuscularly. The surgical eye was dilated with 1% cyclopentolate and 10% phenylephrine; eyelashes were trimmed; and the ocular area was disinfected with povidone iodine. A wire lid speculum was inserted to retract the lids, and a corneal incision was made at 12:00 with a 2.85 mm keratome. Healon 5 was injected to maintain anterior chamber depth and an about 2-3 mm continuous curvilinear capsulorrhexis was performed. A 20 gauge phacoemulsification tip was inserted through the corneal wound and endocapsular lens extraction was performed by phacoemulsification and irrigation/aspiration with BSS mixed with 5% heparin (Solo Pak Lab. Inc., Elk Groove Village, Ill.) and 1.100,000 epinephrine (Anpro Pharmaceutical, Arcadia, Calif.). Considerable care was taken to remove all lens cortical material by diligent irrigation and aspiration. A 4.5 mm silicone plug was inserted into the capsule bag and maneuvered behind the anterior capsulotomy and the polysiloxane polymer material was injected into the capsule bag using a 20 gauge cannula. At the completion of the procedure, the corneal incision was closed with 10-0 nylon sutures and 0.25 ml (20 mg) of gentamicin and 0.1 ml of dexamethasone (2 mg) was injected subconjunctivally every 3 days for two weeks.

The overall positional stability of the silicone plug was evaluated based on the slit lamp observation of placement in the capsule bag. Observations of conjunctiva, corneal pathology, anterior chamber cells, flare and fibrin, posterior synechiae, capsular bag shape, and percent lens regrowth in the capsule bag were recorded.

All slit lamp findings were graded on a scale of 0 to 4 (0=none, 1+=trace, 2+=mild, 3+=moderate, 4+=severe). Throughout the experimental period, rabbits were observed for any abnormal clinical signs, including any abnormal ocular findings such as pain, excessive hyperemia or discharge. Grading of the ocular findings was based on the methods of McDonald and Shadduck (McDonald, T. O., and Shadduck, J. A. Eye Irritation. Advances in Modern Toxicology, Vol. 4, pp. 162-166. Dermatotoxicology and Pharmacology. Eds. Marzulli and Maibach. Washington: Hemisphere, 1977) which is incorporated by reference herein for all that it teaches regarding the grading of ocular findings. All observations were recorded on a Slit Lamp Examination form. Grading for each of these parameters was done as follows:

Cornea: Scores recorded for the cornea reflect the greatest severity of corneal edema/cloudiness observed. Severity of corneal cloudiness was graded as follows:

| None | 0 | Transparent, clear |
| Trace | +1 | Minimal loss of transparency. Only the epithelium and/or the anterior half of the stroma is involved as observed with an optical section of the slit lamp. |
| Mild | +2 | Dull-glass appearance. The cloudiness extends past the anterior half of the stroma. |
| Moderate | +3 | Involvement of the entire thickness of the stroma. The affected stroma has lost its marble-like appearance and is homogeneously white. With optical section, the endothelium is still visible. |
| Severe | +4 | Involvement of the entire thickness of the stroma. With optical section, cannot clearly visualize the endothelium. |

Cells in the anterior chamber: The presence/absence of cells in the anterior chamber was monitored as follows:

| None | 0 | No cells seen |
| Trace | +1 | 1-9 cells per high power field |
| Mild | +2 | Sparse and scattered or localized cells |
| Moderate | +3 | Numerous and scattered and/or clumped cells |
| Severe | +4 | High concentration of cells throughout most or the entire anterior chamber, and/or clumped and cascading down the anterior lens surface |

Anterior chamber flare: Anterior chamber flare was graded on the intensity of the Tyndall phenomenon and was scored by comparing the normal Tyndall effect observed when the slit lamp passes through the lens with that seen in the anterior chamber:

| None | 0 | Absence of visible light beam in the anterior chamber (no Tyndall effect). |
| Trace | +1 | Tyndall beam is barely discernable. The intensity of the light in the anterior chamber is less than the intensity of the light beam as it passes through the lens. |
| Mild | +2 | The Tyndall beam in the anterior chamber is easily discernible and is barely equal in its intensity to the slit beam as it passes through the lens. |
| Moderate | +3 | The Tyndall beam in the anterior chamber is easily discernible and is equal in its intensity to the slit beam as it passes through the lens. |
| Severe | +4 | The Tyndall beam in the anterior chamber is easily discernible and its intensity is greater than the intensity to the slit beam as it passes through the lens. |

Fibrin in the anterior chamber: The presence/absence of fibrin in the anterior chamber was monitored as follows:

| None | 0 | No fibrin seen. |
| Trace | +1 | Minute strands or clumps of fibrin. |
| Mild | +2 | Thin sheet or clumps of fibrin. |
| Moderate | +3 | 20-50% of anterior chamber filled with fibrin. |
| Severe | +4 | Over 50% of anterior chamber filled with fibrin. |

Posterior Synechia: The presence/absence of iris adhesion to the lens capsule is known as posterior synechia and was graded as follows:

| None | 0° | No posterior synechia seen. |
| Trace | 90° | Less or up to 90° of the iris pupil is scarred to the lens capsule (25% of pupil). |
| Mild | 180° | 180° of the iris pupil is scarred to the lens capsule (50% of pupil). |
| Moderate | 270° | 270° of the iris pupil is scarred to the lens capsule (75% of pupil). |
| Severe | 360° | 360° of the iris pupil is scarred to the lens capsule (100% of pupil). |

At the end of the studies, animals were euthanized by an injection of sodium pentobarbital (Eutha-6, Western Medical Supply Co., Inc.) into the marginal ear vein. At all times animals were treated in accordance with USDA guidelines and the ARVO Resolution on the Use of Animals in Research.

Example 1

The study described in Example 1 evaluated: (i) posterior capsule opacification when a foldable silicone IOL in combination with the polysiloxane polymer material is used and (ii) the surgical technique for performing endocapsular extraction through a small 2 mm capsulorrhexis in an older rabbit with a hard lens.

In this study, rabbit 71719 (New Zealand white female; weight 2.4 kg) was 3 months old and rabbits 71565 and 71566 (New Zealand white females; weight 3.5 kg) were 3 years old.

Rabbit 71719 OD, OS: Uneventful endocapsular lens extractions were performed through a 2.0 mm capsulorrhexis using a 20 gauge phaco needle with Healon 5 for anterior chamber maintenance. During phaco, the capsulorrhexis stretched and a 4.5 mm silicone plug was positioned under the capsulorrhexis. In 71719 OD, the polysiloxane polymer material containing a few small bubbles was injected with a 20 gauge cannula on a 3 cc syringe. In 71719 OS, a SI-40NB IOL devoid of haptics was inserted into the capsule bag with the Silver Insertion System and the polysiloxane polymer material was injected into capsule bag in front of the IOL.

Rabbits 71565 and 71566: In these 3 year old large rabbits, the lens nucleus density was estimated to be 3-4+. Endocapsular lens extractions were performed through a 2.0 mm capsulorrhexis using a 21 gauge Shark Tooth Phaco needle with Healon 5 for anterior chamber maintenance. The Phaco time for 71565 OD was 20 minutes. The Phaco time for 71565 OS was 18 minutes. Following lens removal, rabbit 71565 was euthanized. The Phaco time for 71566 OD was 13 minutes. After multiple attempts a 4.5 mm silicone plug was placed under the stretched capsulorrhexis and 0.3 cc of the polysiloxane polymer material was injected into the capsule bag. Slit lamp biomicroscopy was performed on Days 0, 1, 7, 15, 18, 26, 44, 74 and 107.

Results

Immediately postoperative, all wounds were intact. Trace conjunctival injection, corneal haze and edema were noted at day 1 which resolved by one week. Trace anterior chamber flare was seen at day 1-5 which resolved by 2 weeks. Mild posterior synechiae to the capsulorrhexis was seen in all eyes. Severe synechiae was noted in one eye at days 7-26. The anterior capsulorrhexis was sealed by the 4.5 mm silicone plug and/or the Acuvue contact lens throughout the study, except in 2 eyes. In rabbit eye 71719 OS (SI-40 IOL) the polysiloxane polymer material and SI40NB IOL was noted to extrude into the anterior chamber at Day 26.

Results for Rabbit #71719 OD:

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 1 | 1 | 0 | Sil drop | 1 | 0 | 0 | OK | Clear | clear | 1+ haze |
| Day 7 | 0 | 0 | Sil drop | 0 | 0 | 0 | OK | Striae 2+ | clear | 1+ haze |
| Day 15 | 0 | 0 | Sil drop | 0 | 0 | 0 | OK | Striae 2+ | clear | 1+ haze |
| Day 18 | 0 | 0 | Sil drop | 0 | 0 | 15 | OK | Striae 2+ | clear | Limited view |
| Day 26 | 0 | 0 | Sil drop | 0 | 0 | 5 | OK | Striae 2+ | clear | Clear growth ant cap, post cap less clear |
| Day 44 | 0 | 0 | Sil drop | 0 | 0 | 5 | Recessed, clear glob ant to | Large cpx scar | clear | Clear growth ant cap, post cap less clear |
| Day 74 | 0 | 0 | Sil drop | 0 | 0 | 0 | OK | Folds | clear | Clear growth ant cap, post cap less clear |
| Day 107 | 0 | 0 | Sil drop | 0 | 0 | 0 | OK | Linear scar | clear | Clear growth ant cap, post cap 3-4+ opaque |

Results for Rabbit #71719 OS:

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 1 | 1 | 0 | 0 | 1 | 0 | 0 | OK | 0 | clear | Clear IOL |
| Day 7 | 0 | 0 | 0 | 1 | 0 | 300 | OK | 1+ haze, folds | clear | 1+ haze, IOL on pc |
| Day 15 | 0 | 0 | 0 | 0 | 0 | 45 | OK | 1+ haze, folds | clear | 1+ haze, IOL on pc |

-continued

| Days Post OP | Conj | Cornea | AC Cells | AC Flare | AC Fibrin | Post Syn | Patch Position | Anterior Capsule | Poly-siloxane Polymer Clarity | Posterior Capsule |
|---|---|---|---|---|---|---|---|---|---|---|
| Day 18 | 0 | 0 | 0 | 0 | 0 | 20 | OK | scar | clear | 1+ haze, IOL on pc |
| Day 26 | 0 | 0 | NV | NA | NA | 360 | NA | NA | NA | polysiloxane polymer material & IOL in ant chamber |
| Day 44 | 0 | 0 | NV | NA | NA | NA | NA | NA | NA | polysiloxane polymer material & DL in ant chamber |
| Day 74 | 0 | 0 | NV | NA | NA | NA | NA | NA | NA | polysiloxane polymer material & IOL in ant chamber |
| Day 107 | 0 | 0 |  | NA | NA | NA | NA | NA | NA | polysiloxane polymer material & DL in ant chamber |

Results for Rabbit #71566 OD:

| Days Post OP | Conj | Cornea | AC Cells | AC Flare | AC Fibrin | Post Syn | Patch Position | Anterior Capsule | Poly-siloxane Polymer Clarity | Posterior Capsule |
|---|---|---|---|---|---|---|---|---|---|---|
| Day 1 | 1 | 1 | 0 | 1 | 0 | 0 | OK | 0 | clear | Clear with few bubbles |
| Day 7 | 0 | 0 | 0 | 0 | 0 | 5 | OK | 0 | clear | 1+ irregular surface |
| Day 15 | 0 | 0 | 0 | 0 | 0 | 5 | OK | Patchy haze | clear | Folds |
| Day 18 | 0 | 0 | 0 | 0 | 0 | 0 | OK | 1+ haze | clear | 1+ scar |
| Day 26 | 0 | 0 | 0 | 0 | 0 | 0 | OK | Thin patchy growth | clear | Patchy growth, cobble appearance |
| Day 44 | 0 | 0 | 0 | 0 | 0 | 0 | OK | 1 + haze | clear | Lens regrowth surrounds polysiloxane polymer material |
| Day 74 | 0 | 0 | 0 | 0 | 0 | 0 | OK | 1+ haze | clear | 2+ growth, cobble appearance, 2+ haze |
| Day 107 | 0 | 0 | 0 | 0 | 0 | 0 | OK | Sil droplets | clear | 2+ growth, 2+ haze |

Discussion of Example 1 Study Results

Combined Soft Foldable Lens and Polysiloxane Polymer Material

In two separate eyes a SI40NB IOL or an Acuvue contact lens were placed intracapsularly prior to injection of the polysiloxane polymer material, The SI40NB IOL was noted to rest against the posterior capsule and was associated with trace anterior and posterior capsule haze immediately postoperative. As time progressed the polysiloxane polymer material and the SI40NB IOL were extruded into the anterior chamber for no apparent reason. The Acuvue® contact lens was noted to rest against the clear anterior capsule for the two month follow-up period. It is of note that the Acuvue®/polysiloxane polymer material eye had the only clear anterior capsule (devoid of haze, striae or folds) in the 3 studies (see FIGS. 3 and 4). It is possible that direct contact of silicone materials to the capsule and/or lens epithelial cells contributes to capsular haze, striae and/or folds.

Hard Lens Removal Through Small Capsulorrhexis

Three year old large rabbits have a large lens with a nuclear density estimated to be 3-4+. These lenses are thought to be very similar to the adult cataractous lens with a 3-4+ nuclear density. In this study, the hard lens was able to be removed through a 2.0 mm capsulorrhexis using a 21 gauge Shark Tooth Phaco needle. However, the phaco time was exceedingly long, averaging from 13 to 20 minutes. It is important to note that these lenses were much larger than the human lens (maybe as much as twice the size of the human lens) and therefore one would anticipate being able to reduce the total phaco time to 5 to 10 minutes in the human eye.

Example 2

This study evaluated the implantation of an Acuvue® contact lens in combination with the polysiloxane polymer material. The New Zealand white female rabbit (Rabbit 71891) was about 3-4 months old at time of surgery and weighed 2.6 kg.

Rabbit 71891 OD, OS: Uneventful endocapsular lens extractions were performed through a 2.0 (OD) to 2.5 mm (OS) capsulorrhexis using a 20 gauge phaco needle with Healon 5 for anterior chamber maintenance. During phaco the capsulorrhexis stretched and a 4.5 mm silicone plug was positioned under the capsulorrhexis. In the right eye, an Acuvue® contact lens was cut to 6.5 mm and placed into the capsule bag with forceps. The polysiloxane polymer material (0.25 cc) was then injected under the contact lens which assisted the silicone plug in preventing polysiloxane polymer leakage. In the left eye, the polysiloxane polymer material (0.15 cc) was injected into the capsule bag with slight leakage.

Slit lamp biomicroscopy was performed Days 0, 21, 38 and 53. Immediately postoperative, all wounds were intact. Trace to mild corneal haze and edema were noted day 1 and resolved by one week.

Results for Rabbit #71891 OD

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 21 | 0 | 2 | 0 | 0 | 0 | 20 | CL in place | 1 | clear | Striae, 1+ haze |
| Day 38 | 0 | 0 | 0 | 0 | 0 | 10 | CL in place | 0 | clear | 1+ growth, cobble appearance |
| Day 53 | 0 | 0 | 0 | 0 | 0 | 90 | CL in place | 0 | clear | 3+ pco on 100% pc, 3+ opaque |

Results for Rabbit #71891 OS

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 21 | 0 | 1 | 0 | 0 | 0 | 15 | OK | 1+ haze | clear | 2+ striae 1+ haze |
| Day 38 | 0 | 0 | 0 | 0 | 0 | 15 | OK | 1+ haze | clear | 2+ growth 2+ haze |
| Day 53 | 0 | 0 | 0 | 0 | 0 | 90 | OK | 0 | clear | 3+ pco on 100% pc, 3+ opaque |

Example 3

Example 3 was designed to quantitate the amount of polysiloxane polymer material required to fill the capsule bag of 3 month old New Zealand white rabbits. The rabbits used in this study were 3-4 months old and weighed 2.5-2.6 kg.

Rabbits 72823 OD, 72824 OD, 72825 OD: Uneventful endocapsular lens extractions were performed through a 3.0 capsulorrhexis using a 21 gauge phaco needle with Healon 5 for anterior chamber maintenance. A 4.5 mm silicone plug was placed into the capsular bag and 0.2 cc, 0.1 cc and 0.2 cc of the polysiloxane polymer material was injected into the capsule bag of rabbit 72823 OD, 72824 OD and 72825 OD, respectfully. Minimal air bubbles and polysiloxane polymer leakage were noted. Slit lamp biomicroscopy was performed on Days 0, 5, 26 and 57.

Immediately postoperative, all wounds were intact. Trace anterior chamber flare was seen at day 1-5 which resolved by 2 weeks. Mild anterior chamber fibrin was noted in one eye at day 1 and a small polysiloxane polymer material bubble was seen in one eye. In rabbit 72824 OD the silicone plug and polysiloxane polymer material also protruded into the anterior chamber at day 26.

Results for Rabbit #72823 OD

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 5 | 0 | 0 | 0 | 1 | 0 | 0 | OK | 0 | underfilled | Fibrous band at polysiloxane polymer |
| Day 26 | 0 | 0 | 0 | 0 | 0 | 15 | OK | 0 | fair | 2+ growth, cobble 70% of pc |
| Day 57 | 0 | 0 | 0 | 0 | 0 | polysiloxane polymer mat prolapse | moved | 1+ cloudy, 1+ growth | clear | 2+ growth, 2-3+ haze |

Results for Rabbit #72824 OD

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 5 | 0 | 0 | polysiloxane polymer on iris | 1 | 2 | 15 | OK | ?? | clear | |
| Day 26 | 0 | 0 | 0 | 0 | 0 | 15 | Protruding into ac | scars | Protruding into ac | 1+ haze |
| Day 57 | 0 | 0 | NA | NA | NA | NA | NA | NA | Protruding into ac | |

Results for Rabbit #72825 OD

| Days Post OP | Conj | Cornea | AC Cells | AC Flare | AC Fibrin | Post Syn | Patch Position | Anterior Capsule | Polysiloxane Polymer Clarity | Posterior Capsule |
|---|---|---|---|---|---|---|---|---|---|---|
| Day 5 | 0 | 0 | 0 | 1 | 0 | 0 | OK | 0 | clear | Fibrous band at poly-siloxane polymer |
| Day 26 | 0 | 0 | 0 | 0 | 0 | 0 | OK | folds | clear | 1+ growth, cobble |
| Day 57 | 0 | 0 | 0 | 0 | 0 | 5 | OK | 1+ haze | clear | 2+ growth, 2-3+ haze |

Summary of Results

Immediately postoperative, the capsule bags were clear and distended with the clear polysiloxane polymer material. The polysiloxane polymer material used remained clear in all studies throughout the follow-up period (for as long as 107 days). Underfilling of the capsule bag was noted in some eyes. In particular, 0.1 cc of the polysiloxane polymer material was not enough to fill the capsule bag and was associated with slippage of the silicone plug and extrusion of polysiloxane polymer material into the anterior chamber. Rather, about 0.2 cc of polysiloxane polymer material was required to fill the capsule bag of these 3-4 months old New Zealand white rabbits, weighing 2.5-2.6 kg.

Figure 3:
FIGS. 3 and 4 show regenerated lens cells following administration of a polysiloxane polymer used in accordance with the present invention.
Figure 4:

Immediately postoperative, trace posterior capsule haze was noted in most eyes and gradually progressed with striae and folds also noted. Posterior capsule lens regrowth was first noted at day 26 and gradually progressed surrounding the polysiloxane polymer material. In general lens regrowth was clear anterior and peripheral to the polysiloxane polymer material and more irregular and opaque posterior to the polysiloxane polymer material. By one week varying degrees of anterior capsule haze, striae and folds were noted in all eyes except the one eye with the Acuvue® against the anterior capsule (FIGS. 3 and 4).

In summary, the results of the described studies indicated that: (i) endocapsular lens extraction could be performed through a small 2.0 mm capsulorrhexis in the hard lens (3-4+) of 3 year old large rabbits; (ii) a clear anterior capsule devoid of haze, striae or folds was noted in the one eye with the Acuvue® contact lens positioned between the anterior capsule and polysiloxane polymer material; (iii) the polysiloxane polymer material was an intralenticular lens with clear regenerative lens material surrounding it, thus creating a bilenticular lens; and (iv) the 3-4 month old rabbit requires about 0.2 cc of the polysiloxane polymer material to fill the capsule bag.

In one embodiment of the polysiloxane polymers used in accordance with the present invention, the polysiloxane polymer has functional acryl groups that can be obtained from a polymer having the general formula:

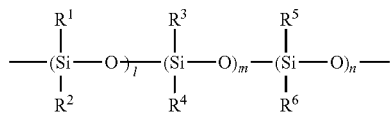

wherein $R^1$ and $R^2$ are independently $C_1$-$C_6$ alkyl; $R^3$ is phenyl; $R^4$ is phenyl or $C_1$-$C_6$ alkyl; $R^5$ is $CF_3(CH_2)_x$ wherein x is 1-5; $R^6$ is $C_1$-$C_6$ alkyl or fluoroalkyl; l is in the molar fraction range of 0 to 0.95; m is in the molar fraction range of 0 to 0.7; and n is in the molar fraction range of 0 to 0.65, the polymer having functional acryl groups at the terminal ends thereof. In one embodiment, m is in the molar fraction range of from greater than 0 to 0.7; and n is in the molar fraction range of from greater than 0 to 0.65.

In another embodiment $R^1$ is methyl, that $R^2$ is methyl, $R^4$ is phenyl, that x is 2, either independently, or in combination. According to these alternatives, in one embodiment $R^6$ is methyl. According to another embodiment, the polysiloxane is a polymer of diphenyl or phenylalkyl siloxane and dialkyl siloxane with terminal acryl groups. According to further embodiments, the polysiloxane is a polymer of diphenyl or phenylalkyl siloxane and trifluoroalkyl(alkyl)siloxane, or a terpolymer or higher order polymer of diphenyl and/or phenylalkyl siloxane, dialkyl siloxane and trifluoroalkyl alkyl siloxane. According to another embodiment, polysiloxane is an acryl-terminated terpolymer of dimethyl siloxane, diphenyl siloxane or phenylmethyl siloxane and 3,3,3-trifluoropropylmethyl siloxane. In certain embodiments the polysiloxanes comprise at least about 4 mol % of trifluoropropylmethyl siloxane and about 1 to about 50 mol % of diphenylsiloxane and/or phenylmethylsiloxane. In other embodiments the polysiloxanes comprise about 4 to about 65 mol % trifluoropropylmethyl siloxane, and about 1 to about 50 mol % of diphenylsiloxaue and dimethylsiloxane monomer units. One suitable acryl-terminated polysiloxane composition comprises about 28 mol % trifluoropropyimethyl siloxane, about 4 mol % diphenyl siloxane and dimethyl siloxane monomer units.

The polysiloxane polymers used in accordance with the present invention are formed into an injectable lens material having a suitable viscosity to be injected through standard cannula with an 18 Gauge needle or finer. For this purpose the material has a viscosity lower than about 60 000 cSt or below about 8000 cSt for being readily injectable through a 21 Gauge needle. The injectable lens material includes at least one type of polysiloxanes according to any of the definitions above. The injectable lens material can also optionally comprise a photoinitiator and/or a crosslinking agent, which itself can be siloxane oligomer or polymer having functional acryl groups and further physiologically or ophthalmologically acceptable additives necessary for producing a lens.

A method of the in vivo production of an IOL, can comprise the steps of preparing an polysiloxane polymer having functional acryl groups; mixing the polymer and a photoinitiator, in one embodiment a medically acceptable blue light photoinitiator, into a composition; injecting the composition into the capsular bag of the eye; and initiating a polymerization reaction to create a lens in the capsular bag. Optionally, the elastomer can also comprise an UV absorbing compound or other conventional additives known to those skilled in the art. A special advantage of the materials used in accordance with the present invention is that the incorporation of a fluoroalkyl siloxane enables materials of high specific gravity to be produced Examples of specific procedures for creating polysiloxane polymers useful in accordance with the present invention can be found in U.S. Pat. No. 6,737,496 which is incorporated by reference herein for all that it teaches regarding creating polysiloxane polymers.

Hyaluronic acid can also be administered in conjunction with the polysiloxane polymers used in accordance with the present invention. Administration of hyaluronic acid can be beneficial in wound healing. Further, fetal wounds that heal without scar formation have an extracellular matrix that is rich in hyaluronic acid. In one embodiment of the present invention, a viscoelastic substance such as hyaluronic acid may be used in conjunction with a polysiloxane polymer for capsule bag filling to enhance the regeneration of lenses following phacoemulsification and subsequent irrigation and aspiration of both the natural and cataractous lens and sealing of the anterior capsule. One skilled in the art will readily appreciate that a variety of high viscosity hyaluronic acid compositions, glycosaminoglycans (GAG's), and/or formulations thereof may be used in accordance with alternate embodiments of the present invention. For example, suitable hyaluronic compositions may include, but are not limited to the following: Restylane® OVD, Perlane® OVD, a variant formulation of Healon® OVD (AB Corp., Sweden), and/or compositions that include high viscosity hyaluronic acid forms such as those described in U.S. Pat. Nos. 6,537,795;

6,090,596; 4,764,360; 6,086,597; 6,368,585; and 5,681,825; U.S. Patent Application Publication No. 2002/0018898 (Ser. No. 09/855,923), and in European Patent Application 0760863 B1, all of which are incorporated herein by reference in their entirety as if fully set forth. Any variant formulation or analogous composition of any of the aforementioned hyaluronic compounds and/or GAGs including, but not limited to hyaluronic acid forms with higher or lower molecular weights, hyaluronic acid forms at variant concentrations, chondroitin sulfate, a hyaluronic acid/chondroitin sulfate mixture, combinations of two or more of the abovementioned compositions, and/or combinations of any of the aforementioned compositions with other suitable agents may be used in accordance with alternate embodiments of the invention. Furthermore, inventive compositions may include a hyaluronic acid compound as well as any number of conventional carriers, additives, preservatives, antibiotics, therapeutic agents and the like that are generally formulated in pharmacological compositions of this nature, as will be readily appreciated by those of skill in the art. Such additional elements may, for example, promote the safety and/or efficacy of the inventive compound. Various quantities, molecular weights, concentrations, and/or forms of hyaluronic acid products may be used to improve the lens cell proliferation and differentiation. For example, a quantity between 0.01 to 3 cc of hyaluronic acid may be used to fill the lens capsule bag to improve the lens cell proliferation and differentiation.

In alternate embodiments, other media can be used individually or in combination to enhance the proliferation and differentiation of lens cells in accordance with the present invention; for instance, amniotic fluid, in vitro fertilization media, growth factors (e.g., BD MATRIGEL™ Basement Membrane Matrix and BD MATRIGEL™ Basement Membrane Matrix High Concentration; BD Biosciences, San Jose, Calif.), and/or other substances that can enhance or control the growth and proliferation of cells will be readily appreciated by one skilled in the art.

In another embodiment, lenticular tissue may be engineered using focal laser photophacocoagulation to remove excess viscoelastic substances and/or modify structure and clarity of the regenerated lens and/or bilenticular lens. As described in U.S. Pat. No. 6,322,556 and U.S. Patent Application Publication Nos. 2002/0103478 (Ser. No. 09/953,121) and 2006/0002981 (Ser. No. 10/881,426) which are all incorporated herein by reference as if fully set forth, laser photophacoablation (laser photoablation) has been used to partially remove ocular tissue (e.g., lens tissue) to correct vision deficiencies and to treat other vision-impairing ocular problems without causing substantial damage to the surrounding tissue regions. In the present invention, laser photophacoablation may be used to remove retained high viscosity or viscoelastic substances in the regenerated lens in combination with the inventive use of hyaluronic acid in combination with polysiloxane polymers.

Lens regeneration can also be enhanced in accordance with the present invention by sealing the anterior capsulotomy with one or more collagen patches. Insertion of a collagen patch may be effected during a procedure for treating ocular disease and/or correcting vision impairment, as for example, endocapsular lens extraction surgery. The lens capsule integrity is restored by inserting one or more collagen patches during endocapsular lens extraction surgery to seal the anterior capsulotomy and restore its continuity, which thereby improves the shape and structure of the regenerated lenses. It will be appreciated by those skilled in the art that a variety of collagen patches may be used and that the sealing of the capsulotomy may occur in various regions in connection with various embodiments of the present invention. For example, a collagen patch that is composed of bovine collagen type IV or a 12 hour collagen shield (Chiron Ophthalmics, Emeryville, Calif., U.S.A.) or a 24 or 72 hour PROSHIELD® Collagen Corneal Shield (Alcon Laboratories, Inc, Fort Worth, Tex.) may be used in accordance with an embodiment of the present invention. Additionally, a collagen patch may be used to seal any opening in the lens capsule bag, not just the anterior capsulotomy. Furthermore, in an alternate embodiment, injectable collagen may be used as a supplement to or a replacement for the inserted collagen patch to further enhance lens regeneration.

In an additional embodiment, collagen may be used as an internal scaffold for lens fiber cell proliferation and differentiation. A variety of collagen-based products may be used, as for example, 25% or 50% suspensions of purified bovine dermis in saline with 0.3% lidocaine (available under the trade name Zyderm I® and Zyderm II® from INAMED Corporation; Santa Barbara, Calif.), monomolecular bovine collagen suspended in solution at 3.5% and 6.5% concentrations (available under the trade name Resoplast® from Rofil Medical International; Breda, Holland), human collagen preparation comprised predominantly of intact collagen fibers as well as other matrix proteins suspended in a neutral pH buffer (available under the trade name Dermalogen® from Collagenesis Corporation; Beverly, Mass.), a cellular human dermal graft processed from tissue bank-derived skin (available under the trade name Alloderm® from LifeCell Corporation; Palo Alto, Calif.), GAG-based compound or polymer; and/or include collagen produced by amnion as described in U.S. Patent Application Publication No. 2004/0048796 (Ser. No. 10/397,867) which is incorporated by reference in its entirety as if fully set forth.

In those embodiments of the present invention directed to methods for treating ocular disease and/or correcting vision impairment, one can use these methods to treat any disease in which enhancing lens regeneration has a beneficial effect on a patient (e.g., ameliorating a disease, lessening the severity of its complications, preventing it from manifesting, preventing it from recurring, merely preventing it from worsening, or a therapeutic effort to effect any of the aforementioned, even if such therapeutic effort is ultimately unsuccessful). Methods of the present invention may be used to treat any diseases which are affected by lens tissue loss or damage, or ocular conditions or impairments which involve a medical procedure comprising the removal or alteration of lens tissue.

The present invention also includes kits. In one embodiment, the kits of the present invention comprise injectable lens materials including, in certain embodiments other materials to assist in the enhancement of lens regeneration. Kits of the present invention can contain one or more of the following in a package or container: (1) one or more injectable lens materials of the present invention; (2) one or more pharmaceutically acceptable adjuvants or excipients; (3) one or more vehicles for administration, such as one or more syringes; (4) one or more tools to use in a surgical procedure; (5) one or more additional bioactive agents for concurrent or sequential administration and/or (6) instructional information. Embodiments in which two or more of components (1)-(6) are found in the same container can also be used.

When a kit is supplied, the different components of the compositions included can be packaged in separate containers and admixed immediately before use. Such packaging of the components separately can permit long-term storage without losing the active components' functions. When more than one composition or active agent is included in a particular kit, the bioactive agents may be (1) packaged separately and admixed separately with appropriate (similar or different) vehicles immediately before use, (2) packaged together and admixed together immediately before use or (3) packaged separately and admixed together immediately before use. If the chosen compounds will remain stable after admixture, however, the admixture need not occur immediately before use but can occur at a time before use, including in one example, minutes, hours, days, months or years before use or in another embodiment at the time of manufacture.

The compositions included in particular kits of the present invention can be supplied in containers of any sort such that the life of the different components are preserved and are not adsorbed or altered by the materials of the container and/or so that other components are not damaged. For example, sealed glass ampules can contain lyophilized agents or variants or derivatives thereof or other bioactive agents, or buffers that have been packaged under a neutral, non-reacting gas, such as, without limitation, nitrogen. Ampules can consist of any suitable material, such as, without limitation, glass, organic polymers, such as, polycarbonate, polystyrene, etc., ceramic, metal or any other material typically employed to hold similar reagents. Other examples of suitable containers include, without limitation, simple bottles that may be fabricated from similar substances as ampules, and envelopes, that can comprise foil-lined interiors, such as aluminum or an alloy. Other containers include, without limitation, test tubes, vials, flasks, bottles, syringes, or the like. Containers can have one or more sterile access ports, such as a bottle having a stopper that can be pierced by a hypodermic injection needle. Other containers may have two compartments that are separated by a readily removable membrane that upon removal permits the components to be mixed. Removable membranes may be, without limitation, glass, plastic, rubber, etc.

As stated earlier, kits can also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device, etc. Detailed instructions may not be physically associated with the kit; instead, a user may be directed to an internet web site specified by the manufacturer or distributor of the kit, or supplied as electronic mail.

As should be understood, the exact formulation, route of administration, and dosage should generally be determined by the attending physician in view of the patient's condition. Dosage amount and interval can be adjusted individually to provide appropriate levels of nucleic acid molecules which are sufficient to maintain therapeutic effect.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A kit for enhancing regeneration of lens cells in a mammal after endocapsular extraction, comprising (i) an injectable polysiloxane polymer lens material having a backbone of general formula:

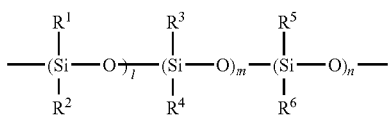

wherein $R^1$ and $R^2$ are independently $C_1$-$C_6$ alkyl; $R^3$ is phenyl; $R^4$ is phenyl or $C_1$-$C_6$ alkyl; $R^5$ is $CF_3(CH_2)_x$, wherein x is 1-5; $R^6$ is $C_1$-$C_6$ alkyl or fluoroalkyl; l is in the molar fraction range of 0 to 0.95; m is in the molar fraction range of from greater than 0 to 0.7; and n is in the molar fraction of from greater than 0 to 0.65, (ii) a visoelastic material which is a cross-linked hyaluronic acid and (iii) hyaluronidase.

2. A kit according to claim 1 wherein said polysiloxane polymer is photocurable.

3. A kit according to claim 1 wherein said kit further comprises a collagen patch.

4. A kit according to claim 1 wherein said kit further comprises an intraocular lens.

5. A kit according to claim 1 wherein said kit further comprises a contact lens polymeric material in the form of a permeable or semi-permeable disc shaped lens.

* * * * *